(12) United States Patent
Yasuno

(10) Patent No.: US 8,748,487 B2
(45) Date of Patent: Jun. 10, 2014

(54) RAW MATERIAL FOR COSMETIC PREPARATION CONTAINING BENZOATE AND COSMETIC PREPARATION CONTAINING SUCH RAW MATERIAL

(75) Inventor: Keiji Yasuno, Kanagawa (JP)

(73) Assignee: The Nisshin Oillio Group, Ltd., Tokyo (JP)

(*) Notice: Subject to any disclaimer, the term of this patent is extended or adjusted under 35 U.S.C. 154(b) by 835 days.

(21) Appl. No.: 11/662,970

(22) PCT Filed: Sep. 6, 2005

(86) PCT No.: PCT/JP2005/016313
§ 371 (c)(1),
(2), (4) Date: Mar. 16, 2007

(87) PCT Pub. No.: WO2006/033231
PCT Pub. Date: Mar. 30, 2006

(65) Prior Publication Data
US 2008/0102044 A1    May 1, 2008

(30) Foreign Application Priority Data
Sep. 21, 2004  (JP) ................. 2004-274085

(51) Int. Cl.
| A61K 8/37 | (2006.01) |
| A61Q 1/06 | (2006.01) |
| A61Q 1/10 | (2006.01) |
| A61Q 17/00 | (2006.01) |
| A61Q 19/00 | (2006.01) |
| A61Q 3/00 | (2006.01) |
| A61Q 5/00 | (2006.01) |

(52) U.S. Cl.
USPC ............ 514/533; 424/59; 424/63; 424/401; 514/506; 514/529; 514/532

(58) Field of Classification Search
None
See application file for complete search history.

(56) References Cited

U.S. PATENT DOCUMENTS

| 3,468,927 A * | 9/1969 | Duke, Jr. et al. ............... 560/128 |
| 4,031,047 A * | 6/1977 | Dhein et al. ............... 528/245.5 |
| 4,218,355 A | 8/1980 | Chang et al. |
| 5,066,484 A | 11/1991 | Castrogiovanni et al. |

(Continued)

FOREIGN PATENT DOCUMENTS

| EP | 0 455 373 A1 | 11/1991 |
| EP | 1 097 699 A1 | 5/2001 |

(Continued)

OTHER PUBLICATIONS

International Search Report dated Dec. 22, 2005. (PCT/ISA/210).
Extended European Search Report dated May 7, 2013.

Primary Examiner — Ernst Arnold
(74) Attorney, Agent, or Firm — McGinn IP Law Group, PLLC

(57) ABSTRACT

Disclosed is a raw material for cosmetic preparations having excellent gloss imparting properties and oxidation stability. Also disclosed is a cosmetic preparation having excellent gloss and feeling of use. The raw material for cosmetic preparations contains an ester compound of (A) benzoic acid, (B) an alcohol selected from the group consisting of neopentyl glycol, dineopentyl glycol, trineopentyl glycol, trimethylolpropane, ditrimethylolpropane, tritrimethylolpropane, dipentaerythritol and tripentaerythritol, and (C) a fatty acid having 3-28 carbon atoms and/or a hydroxycarboxylic acid having 3-28 carbon atoms. The cosmetic preparation contains this raw material for cosmetic preparations.

6 Claims, 1 Drawing Sheet

(1) EXAMPLE 1  (2) EXAMPLE 3  (3) EXAMPLE 5  (4) EXAMPLE 8  (5) EXAMPLE 11
(6) EXAMPLE 12  (7) EXAMPLE 15  (8) COMPARATIVE EXAMPLE 1
(9) COMPARATIVE EXAMPLE 2  (10) COMPARATIVE EXAMPLE 3
(11) COMPARATIVE EXAMPLE 4

(56) References Cited

U.S. PATENT DOCUMENTS

| | | |
|---|---|---|
| 5,145,670 A | 9/1992 | Castrogiovanni et al. |
| 5,145,671 A | 9/1992 | Castrogiovanni et al. |
| 6,160,144 A * | 12/2000 | Bongardt et al. ............. 554/223 |
| 2003/0061969 A1 | 4/2003 | Lee et al. |
| 2003/0065073 A1 | 4/2003 | Lee et al. |
| 2003/0077234 A1 | 4/2003 | Arnaud |
| 2004/0028640 A1 * | 2/2004 | Arnaud et al. ............. 424/70.31 |
| 2007/0041919 A1 | 2/2007 | Yamazaki et al. |

FOREIGN PATENT DOCUMENTS

| | | |
|---|---|---|
| JP | 4-225908 | 8/1992 |
| JP | 2001-172119 | 6/2001 |
| JP | 2002-275024 | 9/2002 |
| JP | 2002-332223 | 11/2002 |
| WO | WO 02/053635 A1 | 7/2002 |
| WO | WO 02/068522 A1 | 9/2002 |
| WO | WO 2005/046625 A1 | 5/2005 |

* cited by examiner

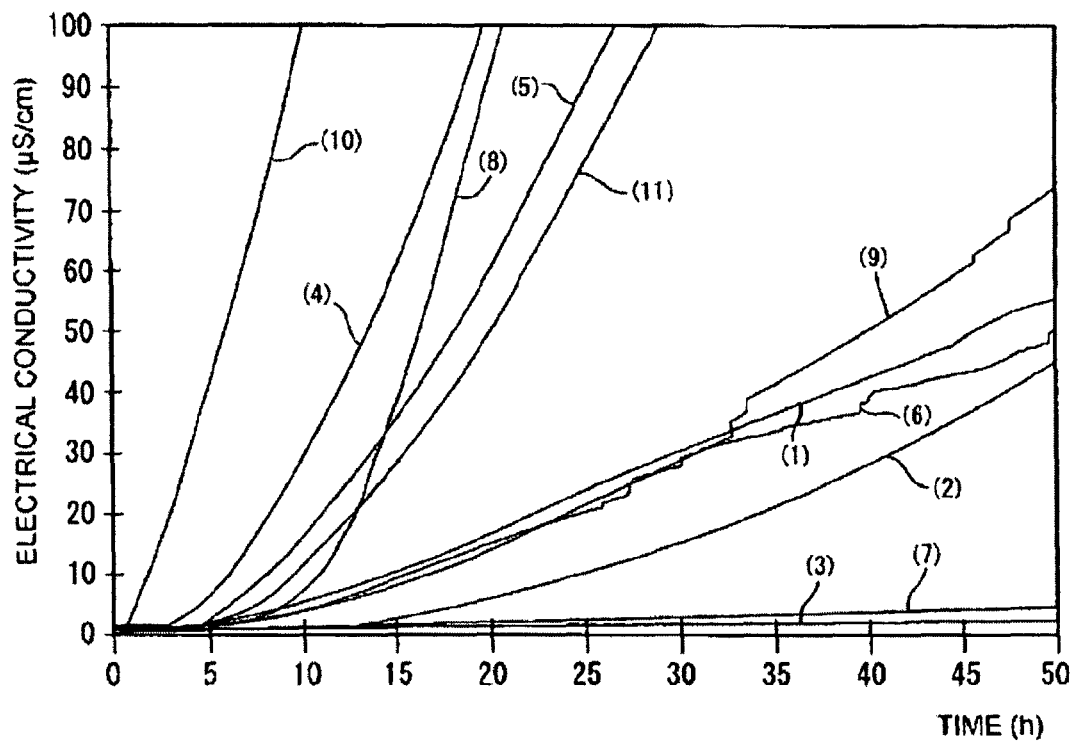
(1) EXAMPLE 1  (2) EXAMPLE 3  (3) EXAMPLE 5  (4) EXAMPLE 8  (5) EXAMPLE 11
(6) EXAMPLE 12  (7) EXAMPLE 15  (8) COMPARATIVE EXAMPLE 1
(9) COMPARATIVE EXAMPLE 2  (10) COMPARATIVE EXAMPLE 3
(11) COMPARATIVE EXAMPLE 4

RAW MATERIAL FOR COSMETIC PREPARATION CONTAINING BENZOATE AND COSMETIC PREPARATION CONTAINING SUCH RAW MATERIAL

TECHNICAL FIELD

The present invention relates to a raw material for cosmetic preparations which contains a benzoate, and to a cosmetic preparation containing the raw material for cosmetic preparations, and, particularly, to a raw material for cosmetic preparations which is superior in gloss imparting characteristics (ability to impart gloss to cosmetic preparations when formulated in cosmetic preparations) and oxidation stability and to a cosmetic preparation which contains the raw material for cosmetic preparations and is superior in glossiness and feeling of use.

BACKGROUND ART

Lanolin is known as a gloss-imparting raw material for cosmetic preparations which is originated from a natural material. However, it is unsatisfactory in view of the stability of qualities and odors because it is derived from an animal material.

Also, as synthetic ester oil agents to be used as gloss-imparting raw materials for cosmetic preparations, various synthetic ester oil agents are widely used. For example, esters of dimer diols and aromatic polycarboxylic acids and hydroxylated fatty acid esters are known as the synthetic ester oil agents (see Japanese Patent Application Laid-Open (JP-A) Nos. 2002-275024 and 2001-172119).

DISCLOSURE OF THE INVENTION

However, it may be said that the foregoing synthetic ester oil agents have been insufficient yet in view of gloss-imparting ability and oxidation stability and both characteristics have been unsatisfied. It is therefore desired to develop a synthetic ester oil agent superior in gloss-imparting ability and oxidation stability.

Accordingly, the present invention relates to a raw material for cosmetic preparations which is superior in gloss-imparting ability and oxidation stability.

Also, the present invention relates to a cosmetic preparation superior in glossiness and feeling of use.

The inventors of the present invention have made earnest studies repeatedly to solve the above problem and as a result, found that a raw material for cosmetic preparations which is superior in gloss-imparting ability and oxidation stability can be obtained from an ester compound of benzoic acid and prescribed alcohol, to complete the present invention.

Accordingly, the present invention relates to a raw material for cosmetic preparations to attain the above object, the raw material comprising an ester compound of the following (A) and (B):

(A) benzoic acid; and
(B) an alcohol selected from the group consisting of neopentyl glycol, dineopentyl glycol, trineopentyl glycol, trimethylol propane, ditrimethylol propane, tritrimethylol propane, dipentaerythritol and tripentaerythritol.

The present invention also relates to a raw material for cosmetic preparations to attain the above object, the raw material comprising an ester compound of the following (A), (B) and (C):

(A) benzoic acid;
(B) an alcohol selected from the group consisting of neopentyl glycol, dineopentyl glycol, trineopentyl glycol, trimethylolpropane, ditrimethylolpropane, tritrimethylol propane, dipentaerythritol and tripentaerythritol; and
(C) a fatty acid having 3 to 28 carbon atoms and/or a hydroxycarboxylic acid having 3 to 28 carbon atoms.

Also, the present invention relates to a cosmetic preparation to attain the above object, the cosmetic preparation comprising the above raw material for cosmetic preparations.

According to the raw material for cosmetic preparations, a raw material for cosmetic preparations which is superior in gloss-imparting ability and oxidation stability can be provided.

Also, according to the cosmetic preparation, a cosmetic preparation having high glossiness and an excellent feeling of use can be provided.

BRIEF DESCRIPTION OF THE DRAWINGS

FIG. 1 is a view showing the results of an oxidation stability test made for examples and comparative examples.

BEST MODE FOR CARRYING OUT THE INVENTION

The present invention will be explained in detail.
(Raw Material for Cosmetic Preparations)

The raw material for cosmetic preparations according to the present invention comprises an ester compound of the following (A) and (B):

(A) benzoic acid; and
(B) an alcohol selected from the group consisting of neopentyl glycol, dineopentyl glycol, trineopentyl glycol, trimethylol propane, ditrimethylol propane, tritrimethylol propane, dipentaerythritol and tripentaerythritol.

Preferably, the raw material for cosmetic preparations comprises an ester compound of (A), (B) and the following (C):

(C) a fatty acid having 3 to 28 carbon atoms and/or a hydroxycarboxylic acid having 3 to 28 carbon atoms.

A raw material for cosmetic preparations which is more superior in oxidation stability can be obtained by using (C) in addition to (A) and (B). Also, an ester compound more resistant to crystallization at ambient temperature can be obtained and a raw material for cosmetic preparations which is superior in handling characteristics can be obtained.

Benzoic acid (A) is used in an amount of 1 to 8 mol based on 1 mol of the alcohol (B). In order to obtain a raw material for cosmetic preparations which is superior in gloss-imparting ability, it is more preferable that the content (%) of benzoic acid in the molecular weight of the intended ester compound be more increased. The content (%) of benzoic acid is preferably 10% or more, more preferably 20% or more, even more preferably 30% or more and even more preferably 33% or more. Here, the content of benzoic acid indicates the ratio of the molecular weight of the benzoic acid residue to the molecular weight of the intended ester compound.

On the other hand, if the content (%) of benzoic acid in the molecular weight of the intended ester compound became excessive, the ester compound is solidified (crystallized). As to the properties of the raw material for cosmetic preparations, the raw material is put more preferably into a paste state-liquid state than into a solid state in view of handling characteristics. Therefore, in the present invention, the content (%) of benzoic acid is preferably 80% or less, more preferably 75% or less, even more preferably 70% or less and even more preferably 65% or less.

Various benzoic acid derivatives, for example, methylbenzoic acid, ethylbenzoic acid and methoxybenzoic acid may be used in place of benzoic acid.

As the alcohol (B), an appropriate one may be selected from the group consisting of neopentyl glycol, dineopentyl glycol, trineopentyl glycol, trimethylol propane, ditrimethylol propane, tritrimethylol propane, dipentaerythritol and tripentaerythritol.

In the present invention, among these compounds, trimethylol propane, ditrimethylol propane, tritrimethylol propane, dipentaerythritol and tripentaerythritol are preferable, and trimethylol propane, ditrimethylol propane and dipentaerythritol are more preferable. Because neopentyl glycol, dineopentyl glycol and trineopentyl glycol tend to solidify (crystallize) at ambient temperature, trimethylol propane and the like are more preferable from the viewpoint of handling characteristics.

In the present invention, at least one OH group in the above alcohol has been esterified by benzoic acid. Also, 80% or more of the OH groups of the above alcohol are preferably esterified by benzoic acid or the component (C) and it is more preferable that all the OH groups be esterified.

The fatty acid (C) having 3 to 28 carbon atoms is preferably a saturated fatty acid having 3 to 28 carbon atoms, more preferably a saturated straight-chain fatty acid having 8 to 22 carbon atoms and a saturated branched fatty acid having 8 to 18 carbon atoms and even more preferably 2-ethylhexanoic acid and isostearic acid.

Also, the hydroxycarboxylic acid (C) having 3 to 28 carbon atoms is preferably a saturated hydroxycarboxylic acid having 3 to 28 carbon atoms, more preferably a saturated hydroxycarboxylic acid having 3 to 18 carbon atoms and even more preferably 12-hydroxystearic acid.

The above (C) fatty acids having 3 to 28 carbon atoms and/or hydroxycarboxylic acids having 3 to 28 carbon atoms are not limited to a single one when used, but may be used as the esterifying raw material in selected combinations of two or more.

The ester compound contained in the raw material for cosmetic preparations according to the present invention is a benzoate represented by the following formulae (1) to (3).

[Formula 1]

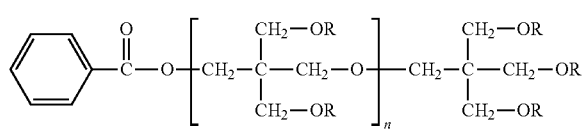

In the formula (1), R represents a hydrogen atom, a benzoic acid residue, a fatty acid residue having 3 to 28 carbon atoms or a hydroxycarboxylic acid residue having 3 to 28 carbon atoms and n denotes an integer from 0 to 2.

[Formula 2]

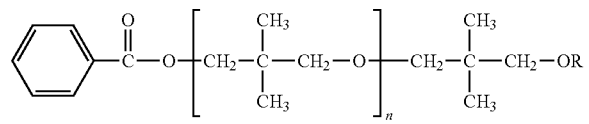

In the formula (2), R represents a hydrogen atom, a benzoic acid residue, a fatty acid residue having 3 to 28 carbon atoms or a hydroxycarboxylic acid residue having 3 to 28 carbon atoms and n denotes an integer from 0 to 2.

[Formula 3]

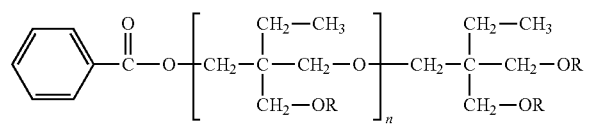

In the formula (3), R represents a hydrogen atom, a benzoic acid residue, a fatty acid residue having 3 to 28 carbon atoms or a hydroxycarboxylic acid residue having 3 to 28 carbon atoms and n denotes an integer of 1 or 2.

There is a correlation between the gloss-imparting ability of the raw material for cosmetic preparations and the refractive index of the ester compound to be contained. With an increase in the refractive index of the ester compound, the gloss-imparting ability of the raw material for cosmetic preparations is increased. Therefore, in the present invention, the refractive index (25° C.) of the above ester compound is 1.48 or more, more preferably 1.49 or more, even more preferably 1.50 or more and even more preferably 1.51 or more. The starting material and conditions are controlled to make the ester compound have such a refractive index (25° C.). In this case, the refractive index may be measured using, for example, an Atsube's refractometer. Also, the raw material for cosmetic preparations may have high refractive indexes ranging widely (for example, 1.48 to 1.54 at 25° C. though depending on the conditions). Therefore, when it is formulated in a cosmetic preparation, the gloss of the cosmetic preparation can be controlled in a wide range, which widens the variation of the cosmetic preparation, resulting an increase in added value.

(Method of Producing a Raw Material for Cosmetic Preparation According to the Present Invention)

In the esterification reaction in the present invention, a reactor is charged with the above raw materials, which are allowed to undergo a reaction at 150° C. to 250° C. for several hours to about 40 hours and preferably several hours to about 30 hours in the presence or absence of an acid, an alkali and a metal catalyst in, preferably, an organic solvent or gas inert to the reaction with removing by-produced water. There is no limitation to the order of the above raw materials to be added in the reaction.

When a catalyst is used, an acid catalyst or an alkoxide of an alkali earth metal is added in an amount of 0.001 to 1.0% by weight based on the weight of the reaction raw materials.

The progress of the above reaction may be rated by measuring the acid value of the solution in the progress of the reaction. After the reaction is finished, there is the case where the reaction solution contains unreacted products. Therefore, these unreacted products are separated by a known method such as washing with water, alkali deoxidation or adsorption treatment to remove them and further subjected to discoloring and deodorizing treatment, thereby purifying the solution.

(Cosmetic Preparation Containing the Raw Material for Cosmetic Preparations According to the Present Invention)

A cosmetic preparation superior in glossiness and feeling of use can be obtained by compounding the raw material for cosmetic preparations according to the present invention in the cosmetic preparation.

Since a cosmetic preparation formulated with the raw material for cosmetic preparations of the present invention is superior in glossiness and feeling of use, it is effective when used for, especially, makeup cosmetics needing glossiness. The raw material for cosmetic preparations is preferably formulated in, for example, lipsticks, eye shadows, hair cosmetics, milky liquids, water-in-oil type hand creams, cream-like oil-in-water type sunscreen cosmetic preparations, manicure preparations, lip creams and lip gloss.

The cosmetic preparation of the present invention may be produced by a usual method. The amount of the raw material for cosmetic preparations is preferably 1 to 80% by weight, more preferably 1 to 60% by weight and even more preferably 1 to 40% by weight though depending on the composition of the benzoate and the type and preparative form of a cosmetic preparation.

The cosmetic preparation of the present invention may be formulated with components such as an oil component, wax, moisture retentive agent, emulsifier, thickener, pigments, perfumes, drugs, ultraviolet absorber, whitening agent, hair tonic and antiperspirant agent according to the need to the extent that the effect of the present invention is not impaired. The cosmetic preparation of the present invention contains the raw material for cosmetic preparations which is superior in gloss-imparting ability and it is therefore possible to reduce the amount of other glazing cosmetic raw materials to be compounded. In this case, though it is unnecessary to formulate these other glazing cosmetic raw materials, they may be formulated in a usual amount.

It is to be noted that the application of the ester compound to be contained in the raw material of cosmetic preparations is not limited to cosmetic preparations and the ester compound may also be used in medical products, quasi-drugs and the like as long as they need gloss.

The present invention will be explained in detail by way of examples, which are not intended to be limiting of the present invention. The numerals (mol) in the parenthesis show a molar ratio.

Reference Example 1

[Preparation of a Raw Material for Cosmetic Preparations which Contains an Ester Compound of Neopentyl Glycol (1.0 mol), and Benzoic Acid (1.0 mol) and 2-ethylhexanoic Acid (1.0 mol)]

A four-neck flask equipped with a stirrer, a temperature gauge, a nitrogen gas blowing tube and a water separator was charged with 78.2 g (1.0 mol) of neopentyl glycol (trade name: NPG PLATELETS, manufactured by EASTMAN CHEMICAL Company), 91.8 g (1.0 mol) of benzoic acid (trade name: PuroxB, manufactured by DSM Company) and 109.0 g (1.0 mol) of 2-ethylhexanoic acid (trade name: Octylic acid, manufactured by Chisso Corporation) and the mixture was reacted using 0.6 g of tin chloride as a catalyst at 180° C. to 200° C. under a nitrogen stream for about 15 hours. After the reaction was finished, the reaction mixture was purified by a usual method, to obtain 150.6 g of the target ester compound of neopentyl glycol, and benzoic acid and 2-ethylhexanoic acid, the ester compound having a saponification value of 335.

Reference Example 2

[Preparation of a Raw Material for Cosmetic Preparations which Contains an Ester Compound of Neopentyl Glycol (1.0 mol) and Benzoic Acid (2.0 mol)]

A four-neck flask equipped with a stirrer, a temperature gauge, a nitrogen gas blowing tube and a water separator was charged with 89.7 g (1.0 mol) of neopentyl glycol (trade name: NPG PLATELETS, manufactured by EASTMAN CHEMICAL Company) and 210.7 g (2.0 mol) of benzoic acid (trade name: PuroxB, manufactured by DSM Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 210.5 g of the target ester compound of neopentyl glycol and benzoic acid, the ester compound having a saponification value of 359.

Reference Example 3

[Preparation of a Raw Material for Cosmetic Preparations which Contains an Ester Compound of Trimethylolpropane (1 mol), and Benzoic Acid (2 mol) and 2-ethylhexanoic Acid (1 mol)]

A four-neck flask equipped with a stirrer, a temperature gauge, a nitrogen gas blowing tube and a water separator was charged with 77.8 g (1.0 mol) of trimethylolpropane (trade name: Trimethylolpropane, manufactured by Celanese Company), 140.2 g (2.0 mol) of benzoic acid (trade name: PuroxB, manufactured by DSM Company) and 82.8 g (1.0 mol) of 2-ethylhexanoic acid (trade name: Octylic acid, manufactured by Chisso Corporation) and the mixture was reacted using 0.6 g of tin chloride as a catalyst at 180° C. to 200° C. under a nitrogen stream for about 15 hours. After the reaction was finished, the reaction mixture was purified by a usual method, to obtain 161.8 g of the target ester compound of trimethylolpropane, and benzoic acid and 2-ethylhexanoic acid, the ester compound having a saponification value of 360.

Reference Example 4

[Preparation of a Raw Material for Cosmetic Preparations which Contains an Ester Compound of Trimethylolpropane (1 mol), and Benzoic Acid (1 mol) and 2-ethylhexanoic Acid (2 mol)]

A four-neck flask equipped with a stirrer, a temperature gauge, a nitrogen gas blowing tube and a water separator was charged with 147.8 g (1.0 mol) of trimethylolpropane (trade name: Trimethylolpropane, manufactured by Celanese Company), 134.6 g (1.0 mol) of benzoic acid (trade name: PuroxB, manufactured by DSM Company) and 317.6 g (2.0 mol) of 2-ethylhexanoic acid (trade name: Octylic acid, manufactured by Chisso Corporation) and the mixture was reacted using 0.6 g of tin chloride as a catalyst at 180° C. to 200° C. under a nitrogen stream for about 15 hours. After the reaction was finished, the reaction mixture was purified by a usual method, to obtain 480 g of the target ester compound of trimethylolpropane, and benzoic acid and 2-ethylhexanoic acid, the ester compound having a saponification value of 344.

Reference Example 5

[Preparation of a Raw Material for Cosmetic Preparations which Contains an Ester Compound of Trimethylolpropane (1 mol), and Benzoic Acid (2 mol) and 12-Hydroxystearic Acid (1 mol)]

A four-neck flask equipped with a stirrer, a temperature gauge, a nitrogen gas blowing tube and a water separator was charged with 59.3 g (1.0 mol) of trimethylolpropane (trade name: Trimethylolpropane, manufactured by Celanese Company), 107.9 g (2.0 mol) of benzoic acid (trade name: PuroxB, manufactured by DSM Company) and 132.8 g (1.0 mol) of 12-hydroxystearic acid (trade name: Hydroxystearic acid, manufactured by Kawaken Fine Chemical Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 160.0 g of the target ester compound of trimethylolpropane, and benzoic acid and 12-hydroxystearic acid, the ester compound having a saponification value of 269.

Reference Example 6

[Preparation of a Raw Material for Cosmetic Preparations which Contains an Ester Compound of Trimethylolpropane (1 mol), and Benzoic Acid (2 mol) and Isostearic Acid (1 mol)]

A four-neck flask equipped with a stirrer, a temperature gauge, a nitrogen gas blowing tube and a water separator was charged with 120.0 g (1.0 mol) of trimethylolpropane (trade name: Trimethylolpropane, manufactured by Celanese Company), 218.5 g (2.0 mol) of benzoic acid (trade name: PuroxB, manufactured by DSM Company) and 261.5 g (1.0 mol) of isostearic acid (trade name: PRISORINE3505, manufactured by Unichema Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 465 g of the target ester compound of trimethylolpropane, and benzoic acid and isostearic acid, the ester compound having a saponification value of 273.

Reference Example 7

[Preparation of a Raw Material for Cosmetic Preparations which Contains an Ester Compound of Trimethylolpropane (1 mol) and Benzoic Acid (3 mol)]

A four-neck flask equipped with a stirrer, a temperature gauge, a nitrogen gas blowing tube and a water separator was charged with 160.8 g (1.0 mol) of trimethylolpropane (trade name: Trimethylolpropane, manufactured by Celanese Company) and 439.2 g (3.0 mol) of benzoic acid (trade name: PuroxB, manufactured by DSM Company), and the mixture was reacted using 0.6 g of tin chloride as a catalyst at 180° C. to 200° C. under a nitrogen stream for about 15 hours. After the reaction was finished, the reaction mixture was purified by a usual method, to obtain 432 g of the target ester compound of trimethylolpropane and benzoic acid, the ester compound having a saponification value of 377.

Reference Example 8

[Preparation of a Raw Material for Cosmetic Preparations which Contains an Ester Compound of Ditrimethylolpropane (1 mol), and Benzoic Acid (3 mol) and 2-ethylhexanoic Acid (1 mol)]

A four-neck flask equipped with a stirrer, a temperature gauge, a nitrogen gas blowing tube and a water separator was charged with 98.7 g (1.0 mol) of ditrimethylolpropane (trade name: Ditrimethylolpropane, manufactured by Perstorp Company), 144.0 g (3.0 mol) of benzoic acid (trade name: PuroxB, manufactured by DSM Company) and 56.8 g (1.0 mol) of 2-ethylhexanoic acid (trade name: Octylic acid, manufactured by Chisso Corporation) and the mixture was reacted using 0.6 g of tin chloride as a catalyst at 180° C. to 200° C. under a nitrogen stream for about 15 hours. After the reaction was finished, the reaction mixture was purified by a usual method, to obtain 162.7 g of the target ester compound of ditrimethylolpropane, and benzoic acid and 2-ethylhexanoic acid, the ester compound having a saponification value of 326.

Reference Example 9

[Preparation of a Raw Material for Cosmetic Preparations which Contains an Ester Compound of Ditrimethylolpropane (1 mol), and Benzoic Acid (2 mol) and 12-Hydroxystearic Acid (2 mol)]

A four-neck flask equipped with a stirrer, a temperature gauge, a nitrogen gas blowing tube and a water separator was charged with 137.0 g (1.0 mol) of ditrimethylolpropane (trade name: Ditrimethylolpropane, manufactured by Perstorp Company), 133.7 g (2.0 mol) of benzoic acid (trade name: PuroxB, manufactured by DSM Company) and 329.3 g (2.0 mol) of 12-hydroxystearic acid (trade name: Hydroxystearic acid, manufactured by Kawaken Fine Chemical Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 440.2 g of the target ester compound of ditrimethylolpropane, and benzoic acid and 12-hydroxystearic acid, the ester compound having a saponification value of 219.

Reference Example 10

[Preparation of a Raw Material for Cosmetic Preparations which Contains an Ester Compound of Ditrimethylolpropane (1 mol), and Benzoic Acid (2 mol) and Isostearic Acid (2 mol)]

A four-neck flask equipped with a stirrer, a temperature gauge, a nitrogen gas blowing tube and a water separator was charged with 139.1 g (1.0 mol) of ditrimethylolpropane (trade name: Ditrimethylolpropane, manufactured by Perstorp Company), 135.8 g (2.0 mol) of benzoic acid (trade name: PuroxB, manufactured by DSM Company) and 325.0 g (2.0 mol) of isostearic acid (trade name: PRISORINE3505, manufactured by Unichema Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 425 g of the target ester compound of ditrimethylolpropane, and benzoic acid and isostearic acid, the ester compound having a saponification value of 223.

Example 11

[Preparation of a Raw Material for Cosmetic Preparations Which Contains an Ester Compound of Dipentaerythritol (1 mol), and Benzoic Acid (3 mol) and 2-ethylhexanoic Acid (3 mol)]

A four-neck flask equipped with a stirrer, a temperature gauge, a nitrogen gas blowing tube and a water separator was charged with 72.4 g (1.0 mol) of dipentaerythritol (trade name: DiPentarit, manufactured by Koei Kagaku Co., Ltd), 104.4 g (3.0 mol) of benzoic acid (trade name: PuroxB, manufactured by DSM Company) and 123.1 g (3.0 mol) of 2-ethylhexanoic acid (trade name: Octylic acid, manufactured by Chisso Corporation) and the mixture was reacted using 0.6 g of tin chloride as a catalyst at 180° C. to 200° C. under a nitrogen stream for about 15 hours. After the reaction was finished, the reaction mixture was purified by a usual method, to obtain 165.7 g of the target ester compound of dipentaerythritol, and benzoic acid and 2-ethylhexanoic acid, the ester compound having a saponification value of 356.

Example 12

[Preparation of a Raw Material for Cosmetic Preparations Which Contains an Ester Compound of Dipentaerythritol (1 mol), and Benzoic Acid (4 mol) and Isostearic Acid (2 mol)]

A four-neck flask equipped with a stirrer, a temperature gauge, a nitrogen gas blowing tube and a water separator was charged with 127 g (1.0 mol) of dipentaerythritol (trade name: DiPentarit, manufactured by Koei Kagaku Co., Ltd), 242.4 g (4.0 mol) of benzoic acid (trade name: PuroxB, manufactured by DSM Company) and 292.6 g (2.0 mol) of isostearic acid (trade name: Isostearic acid, manufactured by Nissan Chemical Industries Ltd.) and the mixture was reacted using 0.6 g of tin chloride as a catalyst at 180° C. to 250° C. under a nitrogen stream for about 38 hours. After the reaction was finished, the reaction mixture was purified by a usual method, to obtain 408.5 g of the target ester compound of dipentaerythritol, and benzoic acid and isostearic acid, the ester compound having a saponification value of 260.

Example 13

[Preparation of a Raw Material for Cosmetic Preparations Which Contains an Ester Compound of Dipentaerythritol (1 mol), and Benzoic Acid (3 mol) and Isostearic Acid (3 mol)]

A four-neck flask equipped with a stirrer, a temperature gauge, a nitrogen gas blowing tube and a water separator was charged with 101.9 g (1.0 mol) of dipentaerythritol (trade name: DiPentarit, manufactured by Koei Kagaku Co., Ltd), 146.8 g (3.0 mol) of benzoic acid (trade name: PuroxB, manufactured by DSM Company) and 351.3 g (3.0 mol) of isostearic acid (trade name: PRISORINE3505, manufactured by Unichema Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 412.9 g of the target ester compound of dipentaerythritol, and benzoic acid and isostearic acid, the ester compound having a saponification value of 241.

Reference Example 14

[Preparation of a Raw Material for Cosmetic Preparations which Contains an Ester Compound of Dipentaerythritol (1 mol), and Benzoic Acid (2 mol) and Isostearic Acid (4 mol)]

A four-neck flask equipped with a stirrer, a temperature gauge, a nitrogen gas blowing tube and a water separator was charged with 91.5 g (1.0 mol) of dipentaerythritol (trade name: DiPentarit, manufactured by Koei Kagaku Co., Ltd), 87.9 g (2.0 mol) of benzoic acid (trade name: PuroxB, manufactured by DSM Company) and 420.6 g (4.0 mol) of isostearic acid (trade name: PRISORINE3505, manufactured by Unichema Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 408.1 g of the target ester compound of dipentaerythritol, and benzoic acid and isostearic acid, the ester compound having a saponification value of 216.

Reference Example 15

[Preparation of a Raw Material for Cosmetic Preparations which Contains an Ester Compound of dipentaerythritol (1 mol), and Benzoic Acid (4 mol) and 12-Hydroxystearic Acid (2 mol)]

A four-neck flask equipped with a stirrer, a temperature gauge, a nitrogen gas blowing tube and a water separator was charged with 56.7 g (1.0 mol) of dipentaerythritol (trade name: DiPentarit, manufactured by Koei Kagaku Co., Ltd), 109.4 g (4.0 mol) of benzoic acid (trade name: PuroxB, manufactured by DSM Company) and 134.1 g (2.0 mol) of 12-hydroxystearic acid (trade name: Hydroxystearic acid, manufactured by Kawaken Fine Chemical Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 166.7 g of the target ester compound of dipentaerythritol, and benzoic acid and 12-hydroxystearic acid, the ester compound having a saponification value of 272.

Reference Example 16

[Preparation of a Raw Material for Cosmetic Preparations which Contains an Ester Compound of dipentaerythritol (1 mol), and Benzoic Acid (3 mol) and 12-Hydroxystearic Acid (3 mol)]

A four-neck flask equipped with a stirrer, a temperature gauge, a nitrogen gas blowing tube and a water separator was charged with 103.3 g (1.0 mol) of dipentaerythritol (trade name: DiPentarit, manufactured by Koei Kagaku Co., Ltd), 144.5 g (3.0 mol) of benzoic acid (trade name: PuroxB, manufactured by DSM Company) and 355.3 g (3.0 mol) of 12-hydroxystearic acid (trade name: Hydroxystearic acid, manufactured by Kawaken Fine Chemical Company) and the mixture was reacted using 0.6 g of tin chloride as a catalyst at 180° C. to 200° C. under a nitrogen stream for about 15 hours. After the reaction was finished, the reaction mixture was purified by a usual method, to obtain 398.1 g of the target ester compound of dipentaerythritol, and benzoic acid and 12-hydroxystearic acid, the ester compound having a saponification value of 238.

Reference Example 17

[Preparation of a Raw Material for Cosmetic Preparations which Contains an Ester Compound of Dipentaerythritol (1 mol), and Benzoic Acid (2 mol) and 12-Hydroxystearic Acid (4 mol)]

A four-neck flask equipped with a stirrer, a temperature gauge, a nitrogen gas blowing tube and a water separator was charged with 89.8 g (1.0 mol) of dipentaerythritol (trade name: DiPentarit, manufactured by Koei Kagaku Co., Ltd), 86.2 g (2.0 mol) of benzoic acid (trade name: PuroxB, manufactured by DSM Company) and 424.0 g (4.0 mol) of hydroxystearic acid (trade name: Hydroxystearic acid, manufactured by Kawaken Fine Chemicals Co., Ltd) and the mixture was reacted using 0.6 g of tin chloride as a catalyst at 180° C. to 200° C. under a nitrogen stream for about 15 hours. After the reaction was finished, the reaction mixture was purified by a usual method, to obtain 391.6 g of the target ester compound of dipentaerythritol, and benzoic acid and 12-hydroxystearic acid, the ester compound having a saponification value of 211.

Comparative Examples 1 to 4

As comparative examples, diisostearyl malate (trade name: Cosmol 222, manufactured by Nisshin OilliO Co., Ltd) (Comparative Example 1), an ester of trimethylol propane (1 mol) and 2-ethylhexanoic acid (3 mol) (Comparative Example 2), an ester of ditrimethylol propane (1 mol) and 2-ethylhexanoic acid (4 mol) (Comparative Example 3) and an ester of dipentaerythritol (1 mol) and 2-ethylhexanoic acid (6 mol) (Comparative Example 4), which were known as a highly glossy raw material for cosmetic preparations were used.

The raw materials and the like used in the above Examples 1 to 17 and Comparative Examples 1 to 4 are described collectively as shown in the following Table 1.

[Table 1]

TABLE 1

Examples 1 to 17 and Comparative Examples 1 to 4

|  | Alcohol (1 mol) | Benzoic acid (mol) | 12-hydroxystearic acid (mol) | Isostearic acid (mol) | 2-ethylhexanoic acid (mol) | Molecular weight | Content of benzoic acid (%) | Properties |
|---|---|---|---|---|---|---|---|---|
| Example 1 | Neopentyl glycol | 1 | 0 | 0 | 1 | 334 | 31.1 | Crystals |
| Example 2 |  | 2 | 0 | 0 | 0 | 312 | 66.7 | Crystals |
| Example 3 | Trimethylolpropane | 2 | 0 | 0 | 1 | 468 | 44.4 | Highly viscous liquid |
| Example 4 |  | 1 | 0 | 0 | 2 | 490 | 21.2 | Highly viscous liquid |
| Example 5 |  | 2 | 1 | 0 | 0 | 624 | 33.3 | Highly viscous liquid |
| Example 6 |  | 2 | 0 | 1 | 0 | 616 | 33.8 | Highly viscous liquid |
| Example 7 |  | 3 | 0 | 0 | 0 | 446 | 70 | Solid when cooled |
| Comparative Example 2 |  | 0 | 0 | 0 | 3 | 512 | 0 | Liquid |
| Example 8 | Ditrimethylolpropane | 3 | 0 | 0 | 1 | 688 | 45.3 | Highly viscous liquid |
| Example 9 |  | 2 | 2 | 0 | 0 | 1022 | 20.4 | Highly viscous liquid |
| Example 10 |  | 2 | 0 | 2 | 0 | 1006 | 20.7 | Highly viscous liquid |
| Comparative Example 3 |  | 0 | 0 | 0 | 4 | 754 | 0 | Liquid |
| Example 11 | Dipentaerythritol | 3 | 0 | 0 | 3 | 944 | 33.1 | Highly viscous liquid |
| Example 12 |  | 4 | 0 | 2 | 0 | 1218 | 34.5 | Highly viscous liquid |
| Example 13 |  | 3 | 0 | 3 | 0 | 1388 | 22.5 | Highly viscous liquid |
| Example 14 |  | 2 | 0 | 4 | 0 | 1558 | 13.4 | Highly viscous liquid |
| Example 15 |  | 4 | 2 | 0 | 0 | 1234 | 33.7 | Highly viscous liquid |
| Example 16 |  | 3 | 3 | 0 | 0 | 1412 | 22.1 | Highly viscous liquid |
| Example 17 |  | 2 | 4 | 0 | 0 | 1590 | 13.1 | Highly viscous liquid |
| Comparative Example 4 |  | 0 | 0 | 0 | 6 | 1010 | 0 | Highly viscous liquid |
| Comparative Example 1 | (Diisostearyl malate) | 0 | 0 | 0 | 0 | 639 | 0 | Highly viscous liquid |

[Measurement of the Refractive Index of the Raw Material for Cosmetic Preparations]

The refractive index of each raw material for cosmetic preparations which were obtained in Examples 1 to 17 according to the present invention and in Comparative Examples 1 to 4 was measured to evaluate its gloss-imparting ability. The higher the refractive index is, the higher the gloss-imparting ability of the raw material for cosmetic preparations is. The refractive index was measured at a temperature of 25° C. by using an Atsube's refractometer (Model: ER-98, manufactured by Elma Hanbai Co., Ltd). The results are shown in Table 2.

TABLE 2

Results of Measurement of Refractive index

|  | Refractive index (25° C.) |
|---|---|
| Example 1 | 1.484 |
| Example 2 | 1.537 |
| Example 3 | 1.517 |
| Example 4 | 1.480 |
| Example 5 | 1.508 |
| Example 6 | 1.505 |
| Example 7 | 1.565 |
| Example 8 | 1.525 |
| Example 9 | 1.493 |
| Example 10 | 1.490 |
| Example 11 | 1.508 |
| Example 12 | 1.519 |
| Example 13 | 1.496 |
| Example 14 | 1.484 |
| Example 15 | 1.514 |
| Example 16 | 1.498 |
| Example 17 | 1.488 |
| Comparative Example 1 | 1.450 |
| Comparative Example 2 | 1.448 |
| Comparative Example 3 | 1.455 |
| Comparative Example 4 | 1.456 |

As is understood from Table 2, it has been clarified that the raw materials for cosmetic preparations obtained in Examples 1 to 17 each exhibited a higher refractive index than those obtained in Comparative Examples 1 to 4, showing that the raw materials for cosmetic preparations obtained in Examples had excellent gloss-imparting ability.

[Test of the Oxidation Stability of the Raw Material for Cosmetic Preparations]

The oxidation stability of each raw material for preparations obtained in Examples 1, 3, 5, 8, 11, 12 and 15 according to the present invention and the oxidation stability of each raw material for preparations obtained in Comparative Examples 1 to 4 were measured by the CDM Test in Standard Oil and Fat Analysis method (Japan Oil Chemical Society). Pure air was fed while heating the sample at 120° C. and volatile decomposed products produced by oxidation were collected in water to measure a change in the conductance of water due to the production of the volatile decomposed products with time. The smaller the change in the conductance of water is, the smaller the decomposed products are, showing that the sample has better oxidation stability. To mention in detail, a change in the electric conductance of each sample was measured using an automatic oil and fats stability tester (trade name: Runshimat 743 model, manufactured by Metrome Company). The results are shown in FIG. 1 and Table 3. The values in Table 3 show the electric conductance (μS/cm) of the sample after 20 hours and the time (h) required for the electric conductance to reach 50 μS/cm.

TABLE 3

Results of Oxidation Stability Test

|  | 120° C., 20 h (μS/cm) | 120° C., 50 μS/cm (h) |
|---|---|---|
| Example 1 | 18 | 45 |
| Example 3 | 6 | 50 |
| Example 5 | 2 | 50 or more |
| Example 8 | 100 | 13.5 |
| Example 11 | 61 | 18 |
| Example 12 | 16 | 50 |
| Example 15 | 2 | 50 or more |
| Comparative Example 1 | 90 | 16 |
| Comparative Example 2 | 15 | 39 |
| Comparative Example 3 | 100 or more | 6 |
| Comparative Example 4 | 51 | 20 |

As is clarified from FIG. 1 and Table 3, the raw material for cosmetic preparations which were obtained in Examples 1, 3, 5, 8, 11, 12 and 15 exhibited stability equal to or higher than Comparative Examples 1 to 4.

Next, a cosmetic preparation to which each raw material for cosmetic preparations which was obtained in Examples 1, 3, 5, 8, 11 and 15 and Comparative Examples 1, 2 and 4 was added was produced and evaluated as the cosmetic preparation.

[Evaluation of the Strength of the Cosmetic Preparation of the Present Invention]

In order to examine the strength of the cosmetic preparation (stick-type rouge) of the present invention, the strength of the cosmetic preparation was evaluated. The evaluation of the strength was made by measuring the bending strength of the cosmetic preparation. The bending strength was measured using a Reometer NRM-2002J (manufactured by Hudo Kogyo Co., Ltd). In the evaluation of the strength of a sample, the case where the sample has a higher strength than the comparative example was rated as ⊙, the case where the sample has a strength equal to the comparative example was rated as ○ and the case where the sample has a lower strength than the comparative example was rated as x.

[Functional Evaluation of the Cosmetic Preparation of the Present Invention]

A functional evaluation was made in the following method to examine the gloss and feeling of use of the cosmetic preparation of the present invention. Ten panelists to be subjected to functional evaluation were allowed to use each cosmetic preparation. Each panelist set an evaluation point based on seven stages according to the following evaluation standard of each functional evaluation item including glossiness. An average of the evaluation points of all panelists was calculated and rated according the standard of four stages.

(Evaluation Based on the Standard of Seven Stages) Evaluation of the Cosmetic Preparation
Evaluation Point: Evaluation
6: Very good
5: Good
4: Slightly good
3: Normal
2: Slightly inferior
1: Inferior
0: Very inferior
(Evaluation in Four Stages) Average of the Evaluation Points of 10 Panelists
Average of the evaluation points in the standard evaluation: evaluation
5 points or more: ⊙ Very excellent
3 points or more and less than 5 points: ○ Excellent
1 point or more and less than 3 points: Δ Indefinable
Less than 1 point: x Particularly inferior Reference Examples 18, Comparative Example 5

[Stick-Type Rouge]

Each stick-type rouge having the formulation shown in Table 4 was produced in the following manner.

Titanium dioxide and a pigment Red 201 were added to a part of the raw material of Example 15, which was then treated using a roller to prepare a pigment part. The remainder part of the raw material for cosmetic preparations which was obtained in Example 15 was mixed with the remainder components shown in Table 4 and dissolved under heating. The obtained solution was added to the above prepared pigment part and the mixture was uniformly dispersed by a homomixer. After the dispersion was poured into a mold, it was cooled quickly to obtain a stick-type rouge (Reference Example 18). A stick-type rouge was produced using the raw material for cosmetic preparations which was obtained in Comparative Example 4 in the same manner as above (Comparative Example 5). The evaluation of the strength and functional evaluation of each lipstick were made and the results are shown in Table 5.

[Table 4]

TABLE 4

Formulation of a stick-type rouge

| | Formulation amount (% by weight) | |
|---|---|---|
| Ingredients | Example 18 | Comparative Example 5 |
| Raw material for cosmetic preparations in Example 15 | 25.0 | — |
| Raw material for cosmetic preparations in Comparative Example 4 | — | 25.0 |
| Titanium dioxide | 5.0 | 5.0 |
| Red No. 201 | 1.8 | 1.8 |
| Candelilla wax | 9.0 | 9.0 |
| Solid paraffin | 8.0 | 8.0 |
| Honey wax | 5.0 | 5.0 |
| Carnauba wax | 5.0 | 5.0 |
| Liquid lanolin | 11.0 | 11.0 |
| Cetyl 2-ethylhexanaote | 20.0 | 20.0 |
| Isopropyl myristate | 10.0 | 10.0 |
| Antioxidant | 0.1 | 0.1 |
| Perfume | 0.1 | 0.1 |
| Total | 100.0 | 100.0 |

TABLE 5

Evaluation of strength and functional evaluation

| | Evaluation of strength | Functional evaluation | |
|---|---|---|---|
| | Bending test | Gloss | Extension |
| Example 18 | ⊙ | ⊙ | ⊙ |
| Comparative Example 5 | ○ | ○ | ○ |

As is understood from Table 5, it was found that the stick-type rouge formulated with the raw material for cosmetic preparations according to the present invention in Example 18 was superior in bending strength and as to the feeling of use of the rouge, it was extended smoothly on the lip and imparted a natural gloss feel. Also, the stick-type rouge of Example 18 had better evaluation results than that obtained in Comparative Example 5 which was prepared by adding dipentaerythritol (1 mol)/2-ethylhexanoic acid (6 mol).

Reference Example 19 and Comparative Example 6

[Eye Shadow Cosmetic]

An eye shadow cosmetic having the formulation shown in Table 6 was produced in the following method.

Titanium oxide, titanium mica, mica, Ultramarine Blue and Black Oxide of iron were added in glyceryl tri-2-ethylhexanoate (trade name: T.I.O, manufactured by Nisshin OilliO Co., Ltd) and the mixture was treated using a roller to prepare a pigment part. The raw material for cosmetic preparations which was obtained in Example 15 was mixed with the remainder components shown in Table 6 and dissolved under heating. The obtained solution was added to the above prepared pigment part and the mixture was uniformly dispersed by a homomixer. After the dispersion was deaerated, it was poured into a mold, which was then cooled quickly to obtain an eye shadow cosmetic (Reference Example 19). An eye shadow cosmetic was produced using the raw material for cosmetic preparations which was obtained in Comparative Example 1 in the same manner as above (Comparative Example 6). Each eye shadow cosmetic was functionally evaluated and the results are shown in Table 7.

TABLE 6

Formulation of an eye shadow cosmetic

| | Formulation amount (% by weight) | |
|---|---|---|
| Ingredients | Example 19 | Comparative Example 6 |
| Raw material for cosmetic preparations in Example 15 | 30.0 | — |
| Raw material for cosmetic preparations in Comparative Example 1 | — | 30.0 |
| Glyceryl tri-2-ethylhexanoate | 10.0 | 10.0 |
| Methylphenylpolysiloxane | 5.0 | 5.0 |
| Ceresine wax | 11.0 | 11.0 |
| Sorbitan sesquioleate | 1.0 | 1.0 |
| Titanium oxide | 2.0 | 2.0 |
| Titanium mica | 3.0 | 3.0 |
| Mica | 15.0 | 15.0 |
| Ultramarine Blue | 20.0 | 20.0 |
| Black Oxide of iron | 2.0 | 2.0 |
| Perfume | 1.0 | 1.0 |
| Total | 100.0 | 100.0 |

TABLE 7

Functional Evaluation

| | Functional evaluation | |
|---|---|---|
| | Gloss | Feel of finish |
| Example 19 | ⊙ | ○ |
| Comparative Example 6 | ○ | ○ |

As is understood from Table 7, the eye shadow cosmetic of Example 19 formulated with the raw material for cosmetic preparations according to the present invention was superior in glossiness and had a good finish feel. Also, the results of evaluation of the eye shadow cosmetic of Example 19 were equal or superior to those of the eye shadow cosmetic of Comparative Example 6 to which diisostearyl malate was added.

Example 20 and Comparative Example 7

[Hair Cosmetic]

A hair cosmetic having the formulation shown in Table 8 was produced in the following method.

The raw material for cosmetic preparations which was prepared in Example 11, liquid paraffin, cetyl isooctanate and reduced lanolin were mixed uniformly. The remainder components were mixed uniformly and the mixture obtained in the previous step was added to and dispersed in the mixture of the reminder components, to obtain a hair cosmetic (Example 20). A hair cosmetic was produced using the raw material for cosmetic preparations which was obtained in Comparative Example 1 in the same manner as above (Comparative Example 7). Each hair cosmetic was functionally evaluated and the results are shown in Table 9.

TABLE 8

Formulation of a hair cosmetic

| | Formulation amount (% by weight) | |
|---|---|---|
| Ingredients | Example 20 | Comparative Example 7 |
| Raw material for cosmetic preparations in Example 11 | 10.0 | — |
| Raw material for cosmetic preparations in Comparative Example 1 | — | 10.0 |
| Liquid paraffin | 5.0 | 5.0 |
| Cetyl isooctanate | 5.0 | 5.0 |
| Reduced lanolin | 2.0 | 2.0 |
| Methylphenylpolysiloxane | 3.0 | 3.0 |
| Alkyl-modified carboxyvinyl polymer | 0.1 | 0.1 |
| Carboxymethyl cellulose | 0.5 | 0.5 |
| Triethanolamine | 0.1 | 0.1 |
| Propylene glycol | 10.0 | 10.0 |
| Antiseptic | 1.0 | 1.0 |
| Purified water | 63.2 | 63.2 |
| Perfume | 0.1 | 0.1 |
| Total | 100.0 | 100.0 |

TABLE 9

Functional Evaluation

| | Functional evaluation | | |
|---|---|---|---|
| | Gloss | Extension | Finish feel |
| Example 20 | ◉ | ◉ | ○ |
| Comparative Example 7 | ○ | ○ | ○ |

As is understood from Table 9, the hair cosmetic of Example 20 formulated with the raw material for cosmetic preparations according to the present invention was lightly extended when applied, had an excellent effect on natural gloss and exhibited smooth hair finish. Also, the results of evaluation of the hair cosmetic of Example 20 were equal or superior to those of the hair cosmetic of Comparative Example 7 to which diisostearyl malate was added.

Reference Example 21 and Comparative Example 8

[Milky Liquid]

A milky liquid having the formulation shown in Table 10 was produced in the following method.

1,3-butylene glycol and PEG 1500 (moisture retentive agent) were added to purified water and the mixture was heated to 70° C. to prepare a water phase. The raw material for cosmetic preparations which was obtained in Example 3 was mixed with oily components to dissolve the both mutually under heating and then, the remainder components were added to the mixture, which was then heated to 70° C. to prepare an oil phase. The water phase was added to the oil phase and the mixture was emulsified using a homomixer to make the emulsion particles uniform, followed by deaeration, filtration and cooling to obtain a milky liquid (Reference Example 21). A milky liquid was produced using the raw material for cosmetic preparations which was obtained in Comparative Example 1 in the same manner as above (Comparative Example 8). Each milky liquid was functionally evaluated and the results are shown in Table 11.

TABLE 10

Formulation of a milky liquid

| | Formulation amount (% by weight) | |
|---|---|---|
| Ingredients | Example 21 | Comparative Example 8 |
| Raw material for cosmetic preparations in Example 3 | 4.0 | — |
| Raw material for cosmetic preparations in Comparative Example 1 | — | 4.0 |
| Stearyl alcohol | 6.0 | 6.0 |
| Stearic acid | 2.0 | 2.0 |
| Squalane | 9.0 | 9.0 |
| Octyldodecanol | 10.0 | 10.0 |
| 1,3-butylene glycol | 6.0 | 6.0 |
| PEG 1500 | 4.0 | 4.0 |
| POE (25) cetyl alcohol ether | 3.0 | 3.0 |
| Glyceryl monostearate | 2.0 | 2.0 |
| Antiseptic | 0.2 | 0.2 |
| Antioxidant | 0.1 | 0.1 |
| Perfume | 0.1 | 0.1 |
| Purified water | 53.6 | 53.6 |
| Total | 100.0 | 100.0 |

TABLE 11

Functional Evaluation

| | Functional evaluation | | |
|---|---|---|---|
| | Gloss | Extension | Flexibility |
| Example 21 | ◉ | ◉ | ◉ |
| Comparative Example 8 | ○ | ○ | ○ |

As is understood from Table 11, it was found that the milky liquid of Example 21 formulated with the raw material for cosmetic preparations according to the present invention provided natural gloss to the skin, was well extended on the skin and provided flexibility to the skin. Also, the results of evaluation of the milky liquid of Example 21 were superior to those of the milky liquid of Comparative Example 8 to which diisostearyl malate was added.

Reference Example 22 and Comparative Example 9

[Water-in-Oil Type Hand Cream]

A water-in-oil type hand cream having the formulation shown in Table 12 was produced in the following method.

The raw material for cosmetic preparations which was prepared in Example 5, squalane, vaseline, octamethylcyclopentasiloxane, cetyl isooctanate and alkyl-containing polyoxyalkylene modified organopolysiloxane were mixed. Silica was added to the mixture to disperse it by a disper-mixer. A mixture obtained by uniformly blending the remainder components was added to and dispersed in the mixture obtained above, to obtain a water-in-oil type hand cream (Reference Example 22). A water-in-oil type hand cream was produced using the raw material for cosmetic preparations which was obtained in Comparative Example 2 in the same manner as above (Comparative Example 9). Each water-in-oil type hand cream was functionally evaluated and the results are shown in Table 13.

TABLE 12

Formulation of a water-in-oil type hand cream

| | Formulation amount (% by weight) | |
|---|---|---|
| Ingredients | Example 22 | Comparative Example 9 |
| Raw material for cosmetic preparations in Example 5 | 30.0 | — |
| Raw material for cosmetic preparations in Comparative Example 2 | — | 30.0 |
| Squalane | 5.0 | 5.0 |
| Vaseline | 1.0 | 1.0 |
| Octamethylcyclopentasiloxane | 10.0 | 10.0 |
| Cetyl isooctanate | 10.0 | 10.0 |
| Alkyl-containing polyoxyalkylene modified organopolysiloxane | 3.0 | 3.0 |
| Silica | 3.0 | 3.0 |
| Ethanol | 5.0 | 5.0 |
| 1,3-butylene glycol | 5.0 | 5.0 |
| Purified water | 27.9 | 27.9 |
| Moisture-retentive component (hyaluronic acid) | 0.1 | 0.1 |
| Total | 100.0 | 100.0 |

Alkyl-containing polyoxyalkylene modified organopolysiloxane ABIL EM-90 (manufactured by Goldschmidt)

TABLE 13

Functional Evaluation

| | Functional evaluation | | |
|---|---|---|---|
| | Gloss | Extension | Flexibility |
| Example 22 | ○ | ⊙ | ⊙ |
| Comparative Example 9 | ○ | ○ | ○ |

As is understood from Table 13, it was found that the water-in-oil type hand cream of Example 22 formulated with the raw material for cosmetic preparations according to the present invention provided gloss to the skin, was smoothly extended on the skin and provided flexibility to the skin. Also, the results of evaluation of the water-in-oil type hand cream of Example 22 were equal or superior to those of the water-in-oil type hand cream of Comparative Example 9 to which trimethylolpropane (1 mol)/2-ethylhexanoic acid (3 mol) was added.

Reference Example 23 and Comparative Example 10

[Cream-Form Oil-in-Water Type Sunscreen Cosmetic]

A cream-form oil-in-water type sunscreen cosmetic having the formulation shown in Table 14 was produced in the following method.

Titanium oxide, cetyl isooctanate, liquid paraffin, sorbitan polyoxyethylene (20 mol) monooleate, sorbitan sesquioleate, stearic acid, cetostearyl alcohol, glyceryl monostearate and a hydrogenated soybean phospholipid were added to the raw material for cosmetic preparations which was obtained in Example 8 and these components were mixed under heating at 70° C. to prepare an oil phase. The remainder components were heated to 70□C to mix uniformly, thereby preparing a water phase. The water phase was added to the oil phase and the mixture was emulsified using a homomixer, followed by deaeration, filtration and cooling to obtain a cream-form oil-in-water type sunscreen cosmetic (Reference Example 23). A cream-form oil-in-water type sunscreen cosmetic was produced using the raw material for cosmetic preparations which was obtained in Comparative Example 1 in the same manner as above (Comparative Example 10). Each cream-form oil-in-water type sunscreen cosmetic was functionally evaluated and the results are shown in Table 15.

[Table 14]

TABLE 14

Formulation of a cream-form oil-in-water type sunscreen cosmetic

| | Formulation amount (% by weight) | |
|---|---|---|
| Ingredients | Example 23 | Comparative Example 10 |
| Raw material for cosmetic preparations in Example 8 | 10.0 | — |
| Raw material for cosmetic preparations in Comparative Example 1 | — | 10.0 |
| Titanium oxide | 10.0 | 10.0 |
| Cetyl isooctanoate | 7.0 | 7.0 |
| Liquid paraffin | 3.0 | 3.0 |
| Sorbitan polyoxyethylene (20 mol) monooleate | 0.7 | 0.7 |
| Sorbitan sesquioleate | 0.3 | 0.3 |
| Stearic acid | 1.0 | 1.0 |
| Cetostearyl alcohol | 1.0 | 1.0 |

TABLE 14-continued

Formulation of a cream-form oil-in-water type sunscreen cosmetic

| | Formulation amount (% by weight) | |
|---|---|---|
| Ingredients | Example 23 | Comparative Example 10 |
| Glyceryl monostearate | 1.0 | 1.0 |
| Hydrogenated soybean phospholipid | 0.5 | 0.5 |
| Perfume | 0.1 | 0.1 |
| Purified water | 54.75 | 54.75 |
| 1,3-butylene glycol | 10.0 | 10.0 |
| Methyl paraoxybenzoate | 0.3 | 0.3 |
| Xanthane gum | 0.2 | 0.2 |
| Sodium hydroxide | 0.15 | 0.15 |
| Total | 100.0 | 100.0 |

TABLE 15

Functional Evaluation

| | Functional evaluation | |
|---|---|---|
| | Gloss | Extension |
| Example 23 | ⊙ | ○ |
| Comparative Example 10 | ○ | ○ |

As is understood from Table 15, it was found that the cream-form oil-in-water type sunscreen cosmetic of Example 23 formulated with the raw material for cosmetic preparations according to the present invention provided natural gloss to the skin and was well extended on the skin when applied to the skin. Also, the results of evaluation of the cream-form oil-in-water type sunscreen cosmetic of Example 23 were equal or superior to those of the cream-form oil-in-water type sunscreen cosmetic of Comparative Example 10 to which diisostearyl malate was added.

Reference Example 24 and Comparative Example 11

[Manicure Preparation]

A manicure preparation having the formulation shown in Table 16 was produced in the following method.

Ethyl acetate, butyl acetate and isopropyl alcohol were added to the raw material for cosmetic preparations which was obtained in Example 1 and these components were mixed uniformly. The remainder components were added to the mixture to mix uniformly, thereby preparing a manicure preparation (Reference Example 24). A manicure preparation was produced using the raw material for cosmetic preparations which was obtained in Comparative Example 1 in the same manner as above (Comparative Example 11). Each manicure preparation was functionally evaluated and the results are shown in Table 17.

TABLE 16

Formulation of a manicure preparation

| | Formulation amount (% by weight) | |
|---|---|---|
| Ingredients | Example 24 | Comparative Example 11 |
| Raw material for cosmetic preparations in Example 1 | 12.0 | — |
| Raw material for cosmetic preparations in Comparative Example 1 | — | 12.0 |
| Nitrocellulose | 13.0 | 13.0 |
| Toluene sulfonamide resin | 2.0 | 2.0 |
| Alkyl acrylate/styrene copolymer | 3.0 | 3.0 |
| Ethyl acetate | 30.0 | 30.0 |
| Butyl acetate | 35.0 | 35.0 |
| Isopropyl alcohol | 5.0 | 5.0 |
| Total | 100.0 | 100.0 |

Alkyl acrylate/styrene copolymer (trade name: Acryl Base MH7057, manufactured by Fujikura Kasei Co., Ltd.

TABLE 17

Functional Evaluation

| | Functional evaluation | |
|---|---|---|
| | Gloss | Extension |
| Example 24 | ⊙ | ⊙ |
| Comparative Example 11 | ○ | ○ |

As is understood from Table 17, it was found that the manicure preparation of Example 24 formulated with the raw material for cosmetic preparations according to the present invention provided gloss to the nail and was well extended on the nail. Also, the results of evaluation of the manicure preparation of Example 24 were equal or superior to those of the manicure preparation of Comparative Example 11 to which diisostearyl malate was added.

The invention claimed is:

1. A raw material for cosmetic preparations, the raw material comprising:
an ester compound represented by formula:

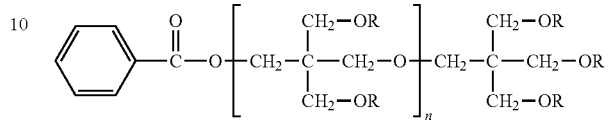

wherein, in the formula, R represents a hydrogen atom, a benzoic acid residue, a saturated fatty acid residue having 3 to 28 carbon atoms, and n denotes an integer of 1 or 2, and wherein the ester compound comprises benzoic acid in a content of 20% or more but 65% or less.

2. The raw material for cosmetic preparations according to claim 1, wherein at least one of the R in formula represents the saturated fatty acid residue having 3 to 28 carbon atoms.

3. The raw material for cosmetic preparations according to claim 1, wherein the saturated fatty acid residue having 3 to 28 carbon atoms comprises 2-ethylhexanoic acid residue or isostearic acid residue.

4. The raw material for cosmetic preparations according to claim 1, wherein the ester compound has a refractive index (25° C.) of 1.49 or more.

5. A cosmetic preparation comprising the raw material of claim 1.

6. The cosmetic preparation according to claim 5, wherein the cosmetic comprises a lipstick, an eye shadow, a hair cosmetic, a milky liquid, a water-in-oil type hand cream, a cream-form oil-in-water type sunscreen cosmetic, or a manicure preparation.

* * * * *